United States Patent [19]

Lewis

[11] Patent Number: 5,071,641

[45] Date of Patent: Dec. 10, 1991

[54] METHOD OF SETTING HAIR

[75] Inventor: David M. Lewis, Otley, Pa.

[73] Assignee: University of Leeds Industrial Services Limited, Leeds, England

[21] Appl. No.: 365,241

[22] Filed: Jun. 12, 1989

[30] Foreign Application Priority Data

Jun. 10, 1988 [GB] United Kingdom ................ 8813728
Jan. 10, 1989 [GB] United Kingdom ................ 8900428

[51] Int. Cl.$^5$ .......................... A61K 7/09; A45D 7/06
[52] U.S. Cl. ...................................... 424/71; 132/203; 132/206; 8/127.51
[58] Field of Search ........................... 424/72, 78, 71; 132/203, 206; 8/127.51

[56] References Cited

U.S. PATENT DOCUMENTS

| | | | |
|---|---|---|---|
| 2,201,929 | 5/1940 | Speakman | 8/127.51 X |
| 2,615,782 | 10/1952 | Haefele | 8/127.51 |
| 2,615,828 | 10/1952 | Haefele | 424/71 |
| 3,227,615 | 1/1966 | Korden | 528/342 X |
| 3,560,609 | 2/1971 | Korden | 424/72 |
| 3,560,610 | 2/1971 | Korden | 424/72 |
| 3,933,421 | 1/1976 | Lewis | 8/128.3 X |
| 3,968,146 | 7/1976 | Lewis | 428/386 X |

Primary Examiner—Thurman K. Page
Assistant Examiner—Susan S. Rucker
Attorney, Agent, or Firm—Darby & Darby

[57] ABSTRACT

A method of setting hair which comprises treating the hair with an aqueous solution of a metal S-thiosulphato-derivative, and curing the derivative. The hair is treated at temperatures of from 15°–60° C. with aqueous solutions containing Bunte salt derivatives, covered with impermeable material, and left to react at from 20°–60° C. before finally rinsing off with water. The permanent setting is as good as with conventional thioglycollate compounds, but the noxious smells associated with the latter are absent.

6 Claims, No Drawings

METHOD OF SETTING HAIR

This invention relates to a method for permanent setting of hair to achieve straightening effects or more usually waving of the hair.

At present, hairdressing salons invariably carry out permanent waving (or for that matter permanent straightening) treatments using formulations containing the alkali salts of the reducing agent thioglycolic acid (usually ammonium or sodium salt); a very slight waving effect is produced if thioglycolates are replaced by sulphites—such treatments are currently used in some market areas but lack the tightness and permanence of curl associated with thioglycolates. Other low molecular weight thiol containing compounds also effectively permanently set hair but are not employed commercially or variety of reasons—toxicology, slower diffusion into the hair, slow rate of reduction and high price being typical.

As mentioned above the greatest disadvantage of using thioglycolates is their very unpleasant odour; attempts are made to mask this problem by using perfumes but nevertheless the malodourous atmosphere makes the hairdressing salon an unpleasant working environment and reduces the customer popularity of such procedures. This invention seeks to reduce or eliminate this problem by replacing thioglycolates or other thiol compounds.

According to the present invention there is provided a method of setting hair which comprises treating the hair with an aqueous solution of a metal S-thiosulphato—derivative, and curing the derivative. S-thiosulphato- derivatives (also known as Bunte salts) useful in the method of the invention include:

$$M^+-O_3SS-(CH_2)_n-COO-M^+ \quad \text{I}$$

where n is 1-6 and M is an alkali metal or ammonium ion. Each M need not be the same.

These compounds have, surprisingly, been shown to effectively replace the usually employed thioglycolic acid salts in permanent waving compositions. The outstanding advantage of these compositions is the substantial absence of noxious thiol odours.

A further advantage is that useful Bunte salts can be readily prepared cheaply—even in situ if desired—from simple starting materials.

The invention may employ polymers which contain multiple Bunte salt residues. Of particular interest are Bunte salt polyamide polymers prepared by the reaction of polyamide epichlorohydrin resins with sodium thiosulphate (Cockett, K. R. F. & Lewis, D. M., J. Soc. Dyers & Col., 92, 399-406 (1976) Schematically the reactive Bunte salt side-chains in the polymers may be written:

$$P-N-CH_2-CH(OH)-CH_2-SSO_3-Na+ \quad \text{II}$$
(P=Polymer)

Other Bunte salt containing polymers of this type may be conveniently prepared by the reaction of sodium thiosulphate with reactive polymers prepared from epichlorohydrin/polyamine condensation; such condensates are available to aftertreat sulphur dyeings on cellulosic materials (e.g. Solidogen IH—Hoechst or Product ES1079—Robinsons).

A particularly useful source of Bunte salt polymers may be to modify naturally available keratins by the well-known oxidative sulphitolysis reaction.

It is envisaged that low molecular weight Bunte salts, for example $M^+-O_3SS-CH_2-CH_2-NH_2$, will be of value in the method of invention.

A preferred compound for use in the method of the invention is 2-S-thiosulphatoethanoic acid, which is closely related to thioglycolic acid and is a very useful Bunte Salt for commercial setting of hair. Its sodium salt may be conveniently prepared as follows:

$$Cl-CH_2-COO-Na^+ + Na_2S_2O_3 \rightarrow Na^+-O_3SS-$$
$$-CH_2-COO-Na^+ + NaCl$$

The above reaction is carried out by dissolving sodium chloroacetate in water adding an aqueous solution of sodium thiosulphate and warming to 50° C.

The process of the invention may employ either low molecular weight Bunte salts, high molecular weight Bunte salts, mono-functional or poly-functional Bunte salt derivatives.

The process is preferably carried out by treating the hair at temperatures of from 15°-60° C., preferably 45°-50° C., with aqueous solutions containing Bunte salt derivatives, covering the hair with impermeable material, leaving the batch to react at from 20°-60° C. and finally rinsing off with water.

Hair Setting Procedures:

When setting hair in the conventional way with ammonium thioglycolate it is normal practice to treat the tresses with a $_p$H9 solution containing 0.5-0.8M thiol (equivalent to 4.6% w/v-7.4% w/v thioglycollic acid) for 15-20 minutes at 20° C. The reduced hair is then rinsed with water and then oxidised with 2.3 %(v/v) hydrogen peroxide for 20 minutes at 20° C.

One method for setting hair with Bunte salt derivatives in the presence of sodium sulphite relies on a wet treatment followed by drying to complete the setting process. Sodium sulphite generates thiol groups from hair keratin; these thiol groups react readily with Bunte salts residues on drying to form mixed disulphides. However it is preferred to use a slightly different setting treatment: the drying step is replaced by a warm (30°-60° C.) 'batching' (15-180 minutes) treatment whereby the rolled-up tresses are covered with polythene (or other impermeable material) to prevent air oxidation and drying out. This has been found to give superior setting results stable to subsequent shampooing.

One method of operating the invention is therefore to treat hair tresses with a solution containing 2-5% (w/v) of the water soluble Bunte salt polymer derivative, (e.g., Formula II), 2% (w/v) sodium sulphite and adjusted to $_p$H 10-11 with ammonium hydroxide. Following complete wetting of the tresses they are combed, individually wound-up on curling rollers and covered with polythene film to prevent drying out. Treatment is continued for 45 minutes at 50° C. The heat may be applied either externally using heated hoods or internally by means of electrically heated curling rollers. After the warm batching period the hair is left to cool for 5 minutes on rollers, rinsed thoroughly with cold water and redried. The degree and permanence of curl produced by this technique is equivalent to the 'conventional' thioglycolate procedure. The hair tresses set by this method have very desirable characteristics, being soft, easily combable, undamaged and unaffected by shampooing.

The invention is illustrated by the following examples:

EXAMPLE 1

A single hair fibre was mounted on a setting frame (J. B. Speakman, J. Soc. Dyers & Col.,52 (1936) 335) stretched to 40% of its original length and then treated for 2 minutes at 50° C. with an aqueous solution of the following compositions:

| | |
|---|---|
| Polymer Bunte Salt II (30% solids) | 60 g/l & 100 g/l |
| Sodium sulphite | 20 g/l |
| Ammonium hydroxide to give pH 11 | |

Following this state the wetted fibre was covered with polythene film and the fibre/frame assembly placed in a laboratory oven for 45 minutes at 50° C. The fibre was then cut from the frame, immersed in water for either half hour or overnight and its length measured and compared to the original. Percentage set retained was calculated:

$$\% \text{ set retention} = \frac{\text{length after setting} - \text{original length}}{1.4 \times \text{original length}} \times 100$$

The results are tabulated in the following table:

| Treatment | 60 g/l Bunte salt | 100 g/l Bunte salt |
|---|---|---|
| original length (mm) | 20.1 | 21.0 |
| extended length (mm) | 29.1 | 29.1 |
| % retention (in air) | 100 | 100 |
| % retention in water (0.5 hr.) | 81 | 88 |
| % retention in water (overnight) | 79 | 84 |

If the Bunte salt, II, was omitted from the above setting composition then a % set retention value, after overnight post-soaking, of 21.8 % was obtained - this value reflecting the setting propensity of sulphite solutions on their own.

EXAMPLE 2
(COMPARATIVE)

The method of example 1 was followed but the following setting composition representative of current hair setting practice was employed:
thioglycolic acid 0.8M (74 g/l)
Ammonium hydroxide to $_p$H 9.3

Treatment was carried out for 20 minutes at 20° C., the fibre rinsed in water in the frame and then oxidised by treatment for 20 minutes at 20° C. with 2.3% (v/v) hydrogen peroxide. The fibre was cut from the frame and the set retention calculated as 72%.

This latter result indicates that the setting propensity of the new Bunte salt system is equivalent to or slightly better than that of the currently practised method.

EXAMPLE 3

Hair tresses were wetted with a solution containing:
Bunte salt polymer II 80 g/l
Sodium sulphite 20 g/l
Ammonium hydroxide to give $_p$H 11
Non-ionic wetting agent 10 g/l The wet hair was wound on rollers, sealed with polythene film and treated for 45 minutes with a hair drier set to give a temperature within the 'batch' of approximately 50° C. The tresses were removed from the rollers and washed well in running cold water. The set or curl obtained was observed to be of a very high degree of tightness and permanence.

By way of comparison similar tresses were set on rollers but this time using a solution containing:
thioglycolic acid 74 g/l
Ammonium hydroxide to $_p$H 9

Treatment was carried out for 20 minutes at 20° C., the tresses rinsed well and then oxidised on the rollers with a 2.3% solution of hydrogen peroxide for a further 20 minutes at 20° C. The tresses were then removed from the rollers and rinsed well in running water. It was observed that the degree and permanence of curl produced was equivalent for both methods.

EXAMPLE 4

A Bunte salt of type given in Formula I above was prepared by dissolving sodium chloroacetate (80 g) in water (500 ml) and adding anhydrous sodium thiosulphate (110g); the solution was warmed to 50° C. whereupon it could be demonstrated that the Bunte salt, disodium 2—S—thiosulphatoethanoic acid, was present in the solution.

Sodium sulphite (20 g) was added to the above solution along
with sufficient water to make up the total volume to 1 liter; the $_p$H of this solution was adjusted to 9 using dilute ammonium hydroxide and the solution could then be employed to set a curl in hair tresses following the methodology described in the first part of Example 3. A significant degree and permanence of curl was obtained from this solution.

I claim:
1. A method of setting hair which comprises:
   treating hair at a temperature of from 15° to 60° C. with an aqueous solution containing:
   from 2 to 5% of at least one compound selected from: $M^+-O_3SS-(CH_2)_n-COO-M^+$ wherein n is 1-6 and M is an alkali metal or ammonium ion; polyamide polymers prepared by the reaction of polyamide epichlorohydrin resins with sodium triosulphate; naturally available keratins modified by oxidative sulphitolysis; $M^+-O_3SS-CH_2-CH_2-NH_2$ wherein M is an alkali metal or ammonium ion; and 2-S-thiosulphatoethanoic acid; and
   2% of sodium sulphite; for a period of from 2 to 45 minutes, said solution being at a pH of from 9 to 11;
   batching said treated hair by covering said treated hair, while still wet from said treatment, with an impermeable material to prevent air oxidation, and drying said treated hair while maintaining a temperature of from 20° to 60° C. for a period of from 15 to 180 minutes;
   cooling and rinsing with cold water said treated hair after the completion of said batching step; and
   drying said rinsed hair, so as to produce a permanent soft curl.
2. A method as claimed in claim 1 in which said compound is:

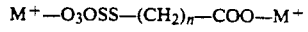

where n is 1–6 and M is an alkali metal or ammonium ion.

3. A method as claimed in claim 1 in which said compound is a polyamide polymer prepared by the reaction of polyamide epichlorohydrin resins with sodium thiosulphate.

4. A method as claimed in claim 1 in which said compound is:

$$M^+ - O_3SS - CH_2 - CH_2 - NH_2.$$

5. A method as claimed in claim 1 in which said compound is a metal or ammonium salt of 2-S-thiosulphatoethanoic acid.

6. A method as claimed in claim 1 in which said treating step includes treating said hair with said solution at a temperature from 45° to 50° C. and said batching step includes maintaining said temperature from 30° to 60° C.

* * * * *